United States Patent [19]

Matson et al.

[11] Patent Number: 4,582,639

[45] Date of Patent: Apr. 15, 1986

[54] ANTITUMOR ANTIBIOTIC COMPOUND

[75] Inventors: James A. Matson; James A. Bush, both of Fayetteville, N.Y.

[73] Assignee: Bristol-Myers Company, New York, N.Y.

[21] Appl. No.: 621,641

[22] Filed: Jun. 18, 1984

[51] Int. Cl.$^4$ ............................................. C07C 103/52
[52] U.S. Cl. ............................................. 260/112.5 R
[58] Field of Search ................................. 260/112.5 R

[56] References Cited

U.S. PATENT DOCUMENTS 4,360,458  11/1982  Koshiyama et al. ......... 260/112.5 R
4,451,456  5/1984  Koshiyama et al. ................. 424/177

OTHER PUBLICATIONS

The Journal of Antibiotics, (1980), 1088–1097, vol. 33.

Primary Examiner—Delbert R. Phillips
Attorney, Agent, or Firm—Aldo A. Algieri

[57] ABSTRACT

A new cyclic depsipeptide antitumor antibiotic designated herein as sandramycin is produced by fermentation of a new microorganism, Nocardioides sp. strain C49,009, ATCC 39419. Sandramycin possesses antibacterial activity and inhibits the growth of tumors in experimental animals.

1 Claim, No Drawings

ANTITUMOR ANTIBIOTIC COMPOUND

SUMMARY OF THE INVENTION

This invention relates to a new cyclic depsipeptide antitumor antibiotic designated herein as sandramycin and to its preparation by fermentation of a new microorganism, Nocardioides species strain C49,009, ATCC 39419, as well as to the pharmaceutical compositions containing the new antitumor antibiotic and methods for using said antitumor antibiotic as an antimicrobial and antitumor agent. This invention also relates to the new microorganism itself, which is employed in the fermentative production of sandramycin.

INFORMATION DISCLOSURE STATEMENT

There is disclosed in U.S. Pat. No. 4,360,458, issued November 23, 1982 to Koshiyama et al., an antitumor antibacterial complex designated BBM-928 and its production by fermentation of a new strain of actinomycetes designated strain G-455-101 (ATCC 31491), which was later determined to be a new species of the genus Actinomadura and designated *Actinomadura luzonensis* nov. sp. [see *J. Antibiotics*, 33(10), 1098–1102 (1980)].

The production, isolation, characterization and antitumor activity of the BBM-928 components are disclosed in *J. Antibiotics*, 33(10), 1087–1097 (1980). The structures of BBM-928A, B, C and D (now called luzopeptin A, B, C and D, respectively) which are the major components of the BBM-928 complex are disclosed in U.S. Pat. No. 4,451,456, issued May 29, 1984 to Koshiyama et al., and have the structural formulae

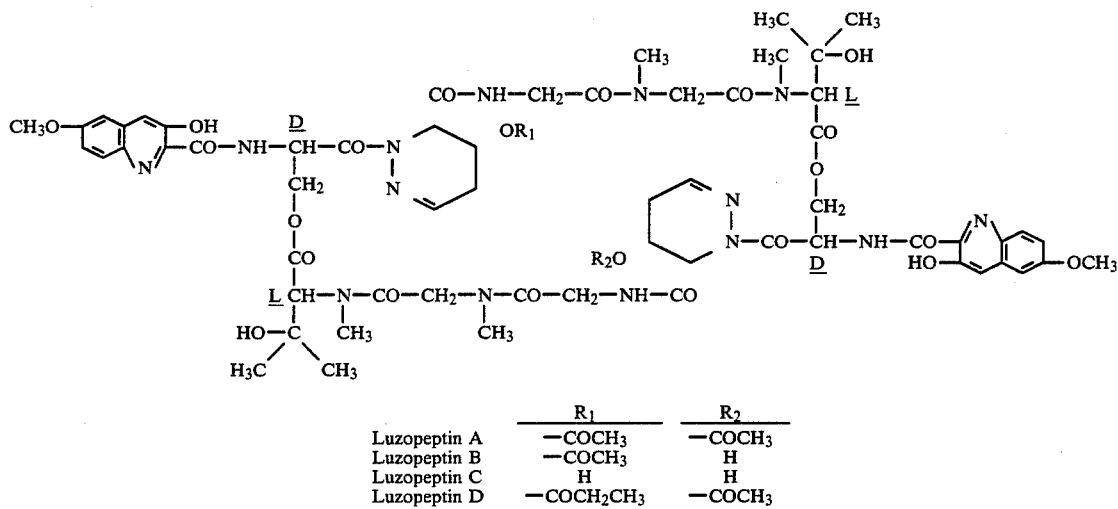

|  | $R_1$ | $R_2$ |
|---|---|---|
| Luzopeptin A | —COCH$_3$ | —COCH$_3$ |
| Luzopeptin B | —COCH$_3$ | H |
| Luzopeptin C | H | H |
| Luzopeptin D | —COCH$_2$CH$_3$ | —COCH$_3$ |

The luzopeptins A, B, C and D contain structural features which include 3-hydroxy-6-methoxyquinaldic acid as the chromophore and 4-hydroxy-2,3,4,5-tetrahydropyridazine-3-carboxylic acid where the structural difference among the three components resides solely in the extent of the acetylation of the hydroxyl group in the tetrahydropyridazine moieties.

DETAILED DESCRIPTION OF THE INVENTION

This invention relates to a new cyclic depsipeptide antitumor antibiotic designated herein as sandramycin having the structural formula

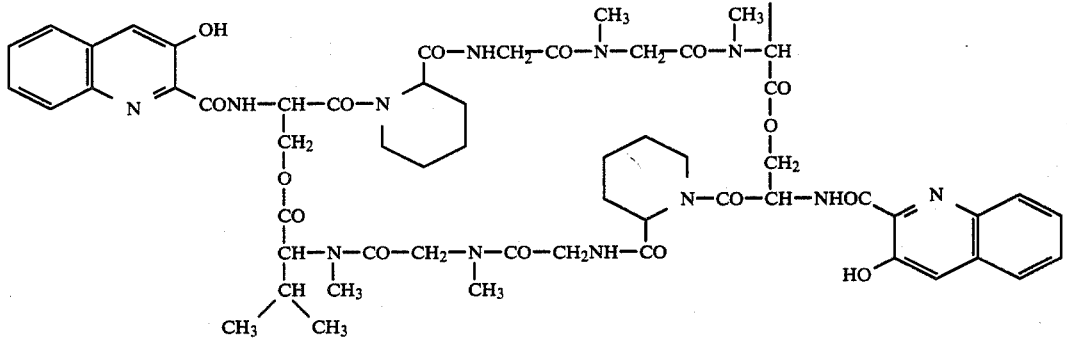

and to the process for the preparation, isolation and purification of sandramycin in substantially pure form.

The novel antibiotic sandramycin is obtained by fermentation of a new microorganism tentatively classified as a species of the genus Nocardioides, accumulating sandramycin produced by said microorganism and collecting the antibiotic sandramycin from the culture broth. A preferred sandramycin-producing microorganism is the Nocardioides sp. strain C49,009 isolated from a soil sample collected in Mexico, and mutants thereof. This strain has been deposited in the American Type Culture Collection, Rockville, Maryland, as ATCC 39419.

THE MICROORGANISM

The following is a general description of the preferred microorganism producing the antitumor antibiotic sandramycin.

MORPHOLOGY

Strain No. C49,009 forms both substrate and aerial mycelia (0.4 μm in width), and the substrate mycelium is long, well-branched and fragmented into short filaments or rods after one week. Strain No. C49,009 tends to lose its ability to form aerial mycelium upon continued cultivation. The hyphae of aerial mycelium branch sparsely. The microscopic observations show that the aerial hyphae are more or less zigzag-shaped at the beginning and develop into long, straight chains of arthrospore-like cylindrical segments (0.5×1 to ~3 μm) which are separated later with translucent hyphae. The surface of spore-like segments is smooth. Strain No. C49,009 is gram-positive and not acid-fast. Sporangium, motile spore and sclerotium are not observed.

CELL WALL COMPOSITION AND WHOLE CELL SUGAR COMPONENTS

The cell wall of Strain No. C49,009 contains LL-diaminopimelic acid and glycine as characteristic amino acid components in the cell wall according to the methods described by B. Becker et al. in Appl. Microbiol., 13, 236–243 (1965) and T. Yamaguchi in *J. Bacteriol.*, 89, 441–453 (1965). Whole cell hydrolyzate shows the presence of glucose, mannose and ribose but lacks any diagnostic sugar as determined according to the procedures outlined by M. P. Lechevalier et al. in *Biol. Actinomycetes Related Organisms*, 11, 78–92 (1976). The aforementioned cell wall composition and whole cell sugar components indicate that Strain No. C49,009 is an actinomycete species of cell wall Type I.

CULTURAL AND PHYSIOLOGICAL CHARACTERISTICS

Strain No. C49,009 is an obligately aerobic actinomycete, and grows well in most descriptive media. The aerial mycelium is formed abundantly or moderately on ISP Medium Nos. 3, 5 and 7, and Czapek's sucrose-nitrate agar, but sparsely on nutritionally-rich organic media such as ISP Medium Nos. 2 and 6, or Bennett's agar. The color of aerial mycelium is white. Melanoid and other distinct pigment are not produced in all descriptive media examined so far. Reverse side color of vegetative mycelium is only yellowish. It shows optimal growth at 28° C., moderate growth at 15° C. and 37° C., but no growth at 5° C. and 45° C. Gelatin and starch are decomposed. Tyrosinase reaction is negative. The growth is inhibited in the presence of 7% NaCl or 0.01% lysozyme. Cultural and physiological characteristics of Strain No. C49,009 are shown in Tables 1 and 2, respectively. Strain No. C49,009 utilizes most sugars for growth, and the utilization of carbon sources is shown in Table 3.

TABLE 1

| Cultural Characteristics of Strain No. C49,009* ** | |
|---|---|
| Tryptone-yeast extract broth: (ISP No. 1) | G: moderate; floccose, faint yellow sediments |
| | D: none |
| Sucrose-nitrate agar (Czapek's agar) | G: abundant |
| | R: yellow white (92)*** to dark grayish yellow (91) |
| | A: moderate, white (263) |
| | D: moderate yellow (87) |
| Glucose-asparagine agar | G: poor |
| | R: yellowish white (92) to pale yellow (89) |
| | A: poor, white (263) |
| | D: none |
| Glycerol-asparagine agar (ISP No. 5) | G: moderate |
| | R: light yellow (86) to moderate yellow (87) |
| | A: moderate, white (263) |
| | D: none |
| Inorganic salts-starch agar (ISP No. 4) | G: moderate |
| | R: pale yellow (89) to moderate yellow (87) |
| | A: poor, white (263) |
| | D: none |
| Tyrosine agar (ISP No. 7) | G: abundant |
| | R: pale yellow (89) to dark yellow (88) |
| | A: moderate, white (263) |
| | D: none |
| Nutrient agar | G: moderate |
| | R: pale yellow (89) |
| | A: moderate, white (263) |
| | D: none |
| Yeast-extract - malt extract agar (ISP No. 2) | G: abundant |
| | R: pale yellow (89) to moderate yellow (87) |
| | A: poor, white (263) |
| | D: none |
| Oat meal agar (ISP No. 3) | G: moderate |
| | R: yellowish white (92) to moderate yellow (87) |
| | A: moderate, white (263) |
| | D: none |
| Bennett's agar | G: moderate |
| | R: pale yellow (89) to dark yellow (88) |
| | A: scant to poor, white (263) |
| | D: none |
| Peptone-yeast extract - iron agar (ISP No. 6) | G: poor |
| | R: pale orange yellow (73) to light orange yellow (70) |
| | A: scant, white (263) |
| | D: none |

*observed after incubation at 28° C. for 3 weeks
**Abbreviation: G = Growth; R = Reverse color; A = aerial mycelium; D = Diffusible pigment
***Color and number in parenthesis follow the color standard in "Kelly, K. L. and D. B. Judd: ISCC-NBS color-name charts illustrated with Centroid Colors. U.S. Dept. of Comm. Cir. 553, Washington, D.C., Nov., 1975".

TABLE 2

| Physiological Characteristics of Strain No. C49,009 | | |
|---|---|---|
| Test | Response | Method or Medium Used |
| Range of temperature for growth | Maximal growth at 28° C. Moderate growth at 15° C. and 37° C. No growth at 5° C. and 45° C. | Bennett's agar |
| Gelatin liquefaction | Liquefied | 1% malt extract, 0.4% yeast extract, 0.4% glucose, 20% gelatin |
| Starch hydrolysis | Hydrolyzed | Starch agar plate |
| Reactions in skimmed milk | Coagulated | Difco skimmed milk |
| Formation of melanoid pigment | Negative | Tyrosine agar, peptone-yeast extract-iron agar and tryptone-yeast extract broth |
| Tyrosinase reaction | Negative | Arai's method* |

TABLE 2-continued

Physiological Characteristics of Strain No. C49,009

| Test | Response | Method or Medium Used |
|---|---|---|
| Nitrate reduction | Negative | Czapek's sucrose-nitrate broth |
| Nitrate reduction | Negative | 0.5% yeast extract, 1% glucose, 0.5% KNO$_3$, 0.1% CaCO$_3$ |
| pH tolerance | Growth at pH 5.0 to pH 10.5. No growth at pH 4.5. | Yeast extract-malt extract agar |
| NaCl tolerance | Growth at 5% NaCl or less. No growth at 7% NaCl. | Basal medium: 1% yeast extract, 2% soluble starch, 1.5% agar |
| Lysozyme tolerance | Sensitive, but partially resistant (growth of a few colonies at 0.01% lysozyme) | Trypticase soy broth plus 1.5% agar |

*Arai, T. and Y. Mikami, "Chromogenicity of Streptomyces", Appl. Microbiol., 23, 402–406 (1972)

TABLE 3

Carbohydrate Utilization of Strain C49,009

| | |
|---|---|
| Glycerol | + |
| D(−)-Arabinose | + |
| L(+)-Arabinose | − |
| D-Xylose | + |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | + |
| Lactose | + |
| Cellobiose | + |
| Melibiose | + |
| Trehalose | + |
| Raffinose | + |
| D(+)-Melezitose | + |
| Soluble starch | + |
| Cellulose | − |
| Dulcitol | − |
| Inositol | + |
| D-Mannitol | + |
| D-Sorbitol | − |
| Salicin | − |

Observed after incubation at 28° C. for 3 weeks.
Basal medium: Pridham-Gottlieb's inorganic medium
Abbreviation:
+: positive utilization,
−: negative utilization

TAXONOMY

Strain No. C49,009 is characterized by its gram-positive reaction, non-acid-fast nature, fragmentation of substrate mycelium, formation of white aerial mycelium, arthrospore-like segmentation in whole parts of aerial mycelium and absence of ability to form any distinct pigment. These characteristics, along with the presence of LL-diaminopimelic acid and glycine, but the absence of diagnostic sugar in the cell wall, place Strain No. C49,009 in the genus Nocardioides [H. Prauser, *Intl. J. Syst. Bacteriol.*, 26, 58–65 (1976)]. Strain No. C49,009 is differentiated from the aerial mycelium-forming nocardioform actinomycetes including *Nocardiopsis dassonvillei*, *Saccharopolyspora hirsuta* and all heterologous species of the genus Nocardia in the diagnostic amino acid or sugar of cell wall and diagnostic physiological properties as described by R. E. Gordon et al., *J. Gen. Microbiol.*, 109, 69–78 (1978) and as shown in Table 4. Strain No. C49,009 is further differentiated from the genus Streptomyces in its sporogenic nocardiae-type morphology; for example, the substrate hyphae of Strain No. C49,009 fragments into short filaments or rods. The arthrospore-like segments of Strain No. C49,009 are distinguishable from the spores of Streptomyces in the site of formation, the arrangement in hyphal sheath and the absence of distinct spore-wall.

TABLE 4

Diagnostic Physiological Characteristics of Strain C49,009

| | |
|---|---|
| Acid fastness | − |
| Decomposition of: | |
| Adenine | − |
| Casein | + |
| Hypoxanthine | − |
| Tyrosine | + |
| Urea | − |
| Xanthine | − |
| Resistance to: | |
| Lysozyme | − |
| Rifampicin | + |
| Hydrolysis of: | |
| Aesculin | + |
| Hippurate | + |
| Starch | + |
| Acid from: | |
| D(−)-Arabinose | + |
| L(+)-Arabinose | − |
| Erythritol | − |
| Glucose | + |
| Inositol | + |
| Lactose | + |
| D-Melezitose | + |
| Melibiose | + |
| Methyl α-glucoside | − |
| Raffinose | + |
| Utilization of: | |
| Benzoate | − |
| Citrate | + |
| Mucate | − |
| Succinate | + |
| Tartrate | − |
| Nitrite from nitrate | − |
| Survival at 50° C., 8 hours | − |

Abbreviation:
+: positive characteristic;
−: negative characteristic

The sensitivity profile to a series of taxon-specific phages distinguishes the strains of the genus Nocardioides from related genera such as Streptomyces or Nocardia [see H. Prauser: Host-phage relationships in nocardioform organisms, "In the Biology of the Nocardiae", Edit. M. Goodfellow et al., London, New York and San Francisco, Academic Press (1976)]. The sensitivity of Strain No. C49,009 to these actinophages was not examined because the phages were not available to us. Based on the cultural and physiological characteristics, the 17 strains of the genus Nocardioides which were isolated from soil samples collected in various districts of the world were placed in a single species, *Nocardioides albus*. Strain No. C49,009 differs from *Nocardioides albus* in its utilization of L-arabinose and inositol, but is similar to the latter in the overall cultural and physiological characteristics. Thus, Strain No. C49,009 was tentatively classified as a species of the genus Nocardioides.

It is to be understood that the present invention is not limited to use of the particular Strain No. C49,009 or to organisms fully answering the above description. It is especially intended to include other sandramycin-producing strains or mutants of the said organism which can be produced from the described organism by known means such as X-radiation, ultraviolet radiation, treatment with nitrogen mustards, phage exposure, and the like.

PRODUCTION OF THE ANTIBIOTIC

Sandramycin is produced by cultivating Nocardioides sp. Strain No. C49,009 (ATCC 39419), or a mutant thereof, in a conventional nutrient medium. The organism is grown in a nutrient medium containing known nutritional sources, i.e., assimilable sources of carbon and nitrogen plus optional inorganic salts and other known growth factors. Submerged aerobic conditions are preferably employed for the production of large quantities of antibiotic, although for production of limited amounts surface cultures and bottles may also be used.

The nutrient medium should contain one or more assimilable carbon sources such as glycerol, glucose, sucrose, mannose, fructose, corn starch, maltose, mannitol, molasses and the like, either in purified or the crude state. The nutrient medium should also contain one or more assimilable nitrogen sources such as, for example, soybean meal, fish meal, malt extract, yeast extract, peptone, gluten meal, cottonseed embryo meal, soy flour, linseed meal, cottonseed flour, casein, hydrolyzed protein substances, nitrates, ammonium salts, urea and the like. Nutrient inorganic salts such as sodium chloride, potassium phosphate, magnesium sulfate, calcium carbonate and trace amounts of heavy metal salts such as copper, zinc, manganese, iron, and the like, may also be added to the nutrient medium.

The fermentation temperature should be in the range of from 15° C. to about 37° C., and preferably in the range of from about 25° C. to about 30° C. The pH of the fermentation medium should be in the range of from about 5 to about 10.5, and the preferred range is from about 6 to about 8.5. Ordinarily, optimum production of sandramycin is obtained in about 2-9 days, depending on the temperature. When tank fermentation is to be carried out, it is desirable to produce a vegetative inoculum in a nutrient broth by inoculating the broth medium with a slant or soil culture, or a lyophilized culture of the microorganism. After obtaining an active inoculum in this manner, it is transferred aseptically to the fermentation tank medium.

ISOLATION OF SANDRAMYCIN

When fermentation is complete, sandramycin is recovered from the culture medium and isolated in a substantially pure form according to the multistep procedure illustrated in the following flow chart.

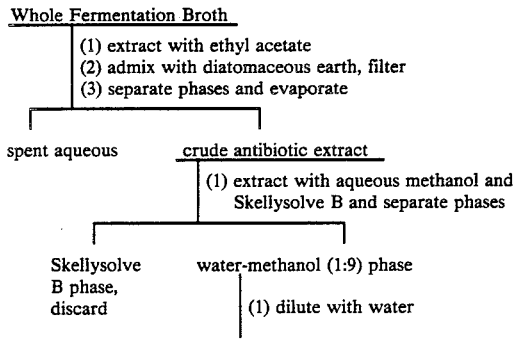

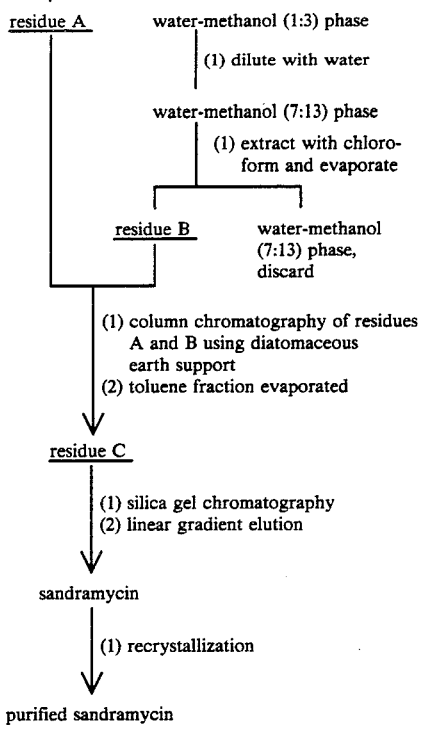

To elaborate on the flow chart, the whole broth from fermentation of Nocardioides sp. Strain No. C49,009 is first extracted with a water-immiscible organic solvent and preferably with ethyl acetate. Filter aid such as Dicalite (tradename of Grefco Inc., Torrance, Ca., for diatomaceous earth) is preferably added to the extraction mixture and the mixture then filtered to remove insolubles. After filtration, the organic phase is separated from the extraction mixture filtrate and concentrated by evaporation to give the crude extract of the said antibiotic. The crude extract is partitioned between an aliphatic hydrocarbon solvent such as Skellysolve B (tradename of Skelly Oil Co. for isomeric hexanes) and about 10% water in methanol. The aqueous methanol phase is diluted with an additional amount of water and the resulting about 25% water in methanol solution is extracted with an organic solvent such as carbon tetrachloride. The aqueous methanol phase is further diluted with water and the resulting about 35% water in methanol solution is extracted with an organic solvent such as chloroform. The carbon tetrachloride extracts are pooled and evaporated in vacuo to give residue A. The chloroform extracts are pooled and evaporated in vacuo to give residue B. Residues A and B can be combined and chromatographed on a column containing diatomaceous earth such as Dicalite using organic solvents of low to high polarity. The appropriate fractions containing the antibiotic are combined and evaporated in vacuo to give residue C. Further purification can be achieved by silica gel low pressure liquid column chromatography of residue C or medium pressure high performance liquid chromatography of residues D, D', E and E' as described below in Example 3, Step C, using a linear gradient of chloroform to 5% methanol in chloroform as the eluant. The appropriate fractions are evaporated to dryness to give sandramycin and recrystallization from an appropriate solvent system yields pure crystalline sandramycin.

STRUCTURE OF SANDRAMYCIN

Sandramycin is a cyclic depsipeptide antitumor antibiotic containing a 3-hydroxyquinoline nucleus as the chromophore and a pipecolic acid moiety. From the spectral and chemical analysis, sandramycin has been determined to have the structural formula

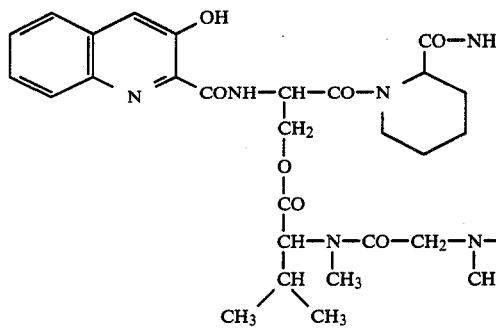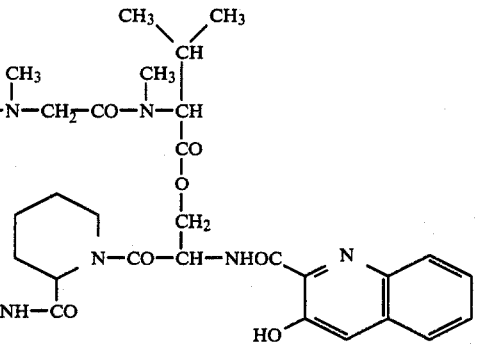

Sandramycin is a white crystalline solid having a melting point of 208°–212° C., a molecular formula of $C_{60}H_{76}O_{16}N_{12}$ and a molecular weight of 1221.3312. It is composed of the elements carbon, hydrogen, nitrogen and oxygen. Elemental analysis data is as follows:

Calc'd. for $C_{60}H_{76}O_{16}N_{12}\cdot 8H_2O$: C, 52.78; H, 6.79; N, 12.31; O (by difference), 28.12 Found: C, 52.58; H, 6.27; N, 12.29; O (by difference), 28.86.

The high resolution mass spectrum of sandramycin was determined with a Kratos MS-50 Spectrometer and FAB ionization. The observed mass is as follows:

Calc'd. for $(M+H)^+$ ion: 1221.5579 Found for $(M+H)^+$ ion: 1221.5571.

The infrared absorption spectrum of sandramycin when pelleted in KBr exhibits characteristic bands at the following frequencies expressed in reciprocal centimeters:

3500, 3340, 2970, 2940, 2880, 1748, 1660, 1640, 1598, 1520, 1468, 1445, 1420, 1336, 1290, 1265, 1235, 1172, 1138, 1092, 1055, 1018, 922, 885, 855 and 838.

The ultraviolet absorption spectrum of sandramycin was determined in methanol (0.01798 g/l) under neutral, acidic and basic conditions. Observed absorption maxima and absorptivities are as follows:

$\lambda_{max}$ in nm (a)

in $CH_3OH$: 356(8.1), 296(7.5), 229(62.8), 217(63.7)

in $CH_3OH$-HCl: 356(8.3), 306(8.1), 228(58.4), 210(62.3)

in $CH_3OH$-NaOH: 395(9.2), 301(7.2), 246(59.8).

A proton magnetic resonance spectrum of sandramycin dissolved in deuterated chloroform was determined with a Bruker Model WM-360 Spectrometer operating at 360 MHz and using tetramethylsilane as the internal standard. The observed chemical shifts (δ values), coupling constants (J values in Hz) and pattern descriptions are as follows:

11.75(s, 2H, Ar-OH), 9.58(d, J=6.39, 2H, ser NH), 8.55(bs, 2H, gly NH), 7.82(bs, 2H, Ar-H[8]), 7.72(m, 2H, Ar-H[5]), 7.63(s, 2H, Ar-H[4]), 7.52(m, 4H, Ar-H[6] and Ar-H[7]), 5.60(m, 2H, αH of pip.), 5.56(d, J=17.58, 2H sar αCH), 5.28(m, 2H, ser αCH), 5.01(d, J=12.79, 2H, ser βCH), 4.88(d, J=12.79, 2H, val αCH), 4.45(bd, J=12.79, 4H, ser βCH and gly αCH), 4.07(bd, J=15.99, 4H, εH of pip. and gly αCH), 3.76(bd, J=12.79, 2H, εH of pip.), 3.58(d, J=17.58, 2H, sar CH), 3.14(s, 6H, N-CH₃), 2.96(s, 6H, N-CH₃), 2.06(m, 2H, val βCH), 1.82(bs, 4H, βCH of pip.), 1.68(bm, 4H, γCH of pip.), 1.57(bm, 4H, δCH of pip.), 0.94(d, J=6.37, 6H, val-CH₃), 0.80(d, J=6.37, 6H, val-CH₃).

A carbon-13 magnetic resonance spectrum of sandramycin dissolved in deuterated chloroform was determined with a Jeol Model FX90Q Spectrometer operating at 22.5 MHz and using tetramethylsilane as the internal standard. The observed chemical shifts (ppm values) wherein each chemical shift represents two carbon atoms, and assignments are as follows:

| No. | Chemical Shift (ppm) | Assignment | |
|---|---|---|---|
| 1 | 171.73 | carbonyl | |
| 2 | 168.54 | carbonyl | |
| 3 | 168.37 | carbonyl | |
| 4,5 | 166.91, 166.91 | carbonyls | |
| 6 | 165.39 | carbonyl | |
| 7 | 153.04 | 3-hydroxyquinoline | C-3 |
| 8 | 140.64 | | C-2 |
| 9 | 133.87 | | C-8a |
| 10 | 131.22 | | C-4a |
| 11 | 128.61 | | C-8 |
| 12 | 127.64 | | C-7 |
| 13 | 126.23 | | C-5 |
| 14 | 125.58 | | C-6 |
| 15 | 119.45 | | C-4 |
| 16 | 61.43 | N—methyl valine | αCH |
| 17 | 27.90 | | βCH |
| 18 | 18.58 | | γCH₃ |
| 19 | 17.82 | | γCH₃ |
| 20 | 29.42 | | NCH₃ |
| 21 | 49.79 | glycine | αCH₂ |
| 22 | 41.02 | sarcosine | αCH |
| 23 | 34.08 | | N—CH₃ |
| 24 | 51.74 | serine | αCH |
| 25 | 61.11 | | βCH₂ |
| 26 | 48.49 | pipecolic acid | αCH |
| 27 | 27.90 | | β-CH₂ |
| 28 | 19.34 | | γ-CH₂ |
| 29 | 24.11 | | δ-CH₂ |
| 30 | 43.07 | | ε-CH₂ |

The key structural features of sandramycin which distinguishes it from the luzopeptins A, B and C are the presence of 3-hydroxyquinaldic acid and pipecolic acid moieties instead of the 3-hydroxy-6-methoxyquinaldic acid and the 4-substituted-tetrahydropyridazine-3-carboxylic acid groups, respectively.

BIOLOGICAL ACTIVITY OF SANDRAMYCIN

The antibacterial activities of sandramycin were determined by a serial two-fold agar dilution method. The results are shown in Table 5 in comparison with the activities of luzopeptin A and echinomycin. As is seen from Table 5, sandramycin is strongly inhibitory to the gram-positive organisms such as *Bacillus subtilis* and *Staphylococcus aureus* as well as to *Streptococcus faecalis*.

TABLE 5

Antimicrobial Activity of Sandramycin

| Test Organism | Minimum Inhibitory Concentration (MIC) (mcg/ml) | | |
|---|---|---|---|
| | Sandramycin | Luzopeptin A | Echinomycin |
| *B. subtilis* (Rec. +) A22508-2 | 0.024 | 0.195 | 0.049 |
| *B. subtilis* (Rec. −) A22509-2-2 | 0.012 | 0.049 | <0.003 |
| *S. aureus* 209P-A9497 | 0.012 | 0.098 | 0.012 |
| *S. aureus* (echinomycin resistant) A9628 | 0.098 | 0.098 | 0.78 |
| *Strep. faecalis* A9611 | 0.024 | 0.195 | 0.012 |
| *E. coli* A15119 | 12.5 | 12.5 | 12.5 |
| *E. coli* (actinomycin sensitive) A21780 (AS-19) | 12.5 | 12.5 | 6.25 |

Sandramycin was also tested against the transplantable mouse tumor P-388 leukemia, and the results are shown in Table 6. The methodology used generally followed the protocols of the National Cancer Institute [Cancer Chemotherapy Rep. Part 3, 3, 1-103 (1972)]. The essential experimental details are given at the bottom of Table 6. Two different dose regimens were tested: single dose on day 1 and daily for 5 days. With both schedules, the optimum dose appears to be about 0.2 mg/kg/injection.

TABLE 6

Effect of Sandramycin on P-388 Leukemia

| Compound | Treatment Schedule | Dose, IP mg/kg/inj. | MST days | Effect MST % T/C | AWC gm Day 4 | Survivors Day 5 |
|---|---|---|---|---|---|---|
| Sandramycin | d. 1 | 3.2 | Toxic | Toxic | −2.8 | 0/6 |
| | | 1.6 | 11.5 | 128 | −1.3 | 6/6 |
| | | 0.8 | 10.0 | 111 | −1.6 | 6/6 |
| | | 0.4 | 11.0 | 122 | −0.7 | 6/6 |
| | | 0.2 | 14.5 | 161 | −1.4 | 6/6 |
| | | 0.1 | 11.0 | 122 | −0.9 | 6/6 |
| | | 0.05 | 10.0 | 111 | −0.6 | 6/6 |
| | | 0.025 | 9.5 | 106 | −0.2 | 6/6 |
| Sandramycin | d. 1→5 | 1.6 | Toxic | Toxic | −1.7 | 2/6 |
| | | 0.8 | 6.0 | 67 | −1.4 | 5/6 |
| | | 0.4 | 11.0 | 122 | −1.3 | 6/6 |
| | | 0.2 | 12.0 | 133 | −1.7 | 5/6 |
| | | 0.1 | 11.5 | 128 | −0.8 | 6/6 |
| | | 0.05 | 8.5 | 94 | −1.8 | 6/6 |
| | | 0.025 | 10.0 | 111 | −1.4 | 5/5 |
| | | 0.0125 | 10.5 | 117 | −0.9 | 6.6 |
| Control | | Saline | 9.0 | — | 0.2 | 10/10 |

Tumor inoculum: $10^6$ ascites cells implanted i.p.
Host: $CDF_1$ female mice
Evaluation: MST=median survival time
Effect: % T/C≧(MST treated/MST control)×100
Criteria: % T/C=125 considered significant antitumor activity
AWC: average weight change (treated-control) in grams (on day 4)

As indicated by the antimicrobial and mouse tumor data provided above, sandramycin is useful as an antibiotic and also as an antitumor agent for inhibition of mammalian malignant tumors such as P-388 leukemia.

The invention includes within its scope pharmaceutical compositions containing an effective antimicrobial or tumor-inhibiting amount of sandramycin in combination with an inert pharmaceutically acceptable carrier or diluent. Such compositions may also contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent, the sandramycin or pharmaceutical composition thereof is administered so that the concentration of active ingredient is greater than the minimum inhibitory concentration for the particular organism being treated. For use as an antitumor agent, optimal dosages and regimens of sandramycin for a given mammalian host can be readily ascertained by those skilled in the art. It will, of course, be appreciated that the actual dose of sandramycin used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention. Skellysolve B is a commercially available petroleum solvent (Skelly Oil Co.) comprising isomeric hexanes and having a boiling point of 60°-69° C. Dicalite is diatomaceous earth manufactured by Grefco, Inc., Torrance, California. Unless otherwise indicated, all temperatures below are in degrees Centigrade.

EXAMPLE 1

Fermentation of Sandramycin

A. Shake-flask Fermentation

Nocardioides sp. Strain No. C49,009, ATCC 39419, was maintained and transferred in culture test tubes on agar slants of yeast-malt extract agar. This medium consists of 4.0 g glucose, 4.0 g yeast extract, 10.0 malt extract and 20.0 g agar made up to one liter with deionized water. With each transfer the agar slant culture was incubated for seven days at 27° C. To prepare an inoculum for the production phase, mycelial growth from the slant culture was transferred to a 500 ml Erlenmeyer flask containing 100 ml of sterile medium consisting of 30.0 g glucose, 10.0 g soy flour, 10.0 g cottonseed embryo meal and 3.0 g CaCO$_3$ made up to one liter with deionized water. This vegetative culture was incubated at 27° C. for 48 hours on a Gyrotory tier shaker (Model G53, New Brunswick Scientific Co., Inc.) set at 210 rev./min. describing a circle with a 5.1 cm diameter. Four ml of vegetative culture was transferred to a 500 ml Erlenmeyer flask containing 100 ml of sterile production medium consisting of 20.0 g sucrose, 10.0 g soy flour, 10.0 g linseed meal and 5.0 g CaCO$_3$ made up to one liter with deionized water. The production culture was incubated at 27° C. on a shaker such as used for the vegetative culture set at 250 rev./min. At 96 hours the production culture was harvested for the isolation of sandramycin.

B. Bench-top Fermentation

For production of sandramycin in a bench-top fermentor, 400 ml of vegetative culture as described in Example 1A was transferred to a fermentor (Microgen Model SF-116, New Brunswick Scientific Co., Inc.) with 10 liters of production medium consisting of 40 g corn starch, 20 g linseed meal, 1 g (NH$_4$)$_2$SO$_4$ and 5 g CaCO$_3$ per liter of deionized water. The temperature was maintained at 27° C., the agitation rate was 300 rev./min. and the air flow rate was 8 liters/min. After 202 hours of incubation, sandramycin was isolated from the culture.

C. Tank Fermentation

For pilot plant production of sandramycin, 2 liters of vegetative culture (prepared according to the general procedure of Example 1A) was transferred to a fermentor containing 30 liters of production medium consisting of 40 g of corn starch, 20 g linseed meal, 1 g (NH$_4$)$_2$SO$_4$ and 5 g CaCO$_3$ per liter of deionized water. The incubation temperature was 26.5° C., the air flow rate was 80 liters/min., the agitation rate was 375 rev./min. and the back pressure was 1 atmosphere. After 183 hours, the tank fermentation was harvested for the isolation of sandramycin.

EXAMPLE 2

Isolation and Purification of Sandramycin

Step A: Extraction

Raw fermentation whole broth (~8 liters) was transferred to a 20-liter polyethylene tank (48 cm diameter top, 44 cm diameter bottom, 55 cm high) equipped with a faucet at the bottom. An equal volume of ethyl acetate was added. The mixture was stirred with an air driven stirrer at a good mixing speed for 30 minutes. Approximately 6 liters (2 kg) of Dicalite was added and mixed. The mixture was filtered on a Dicalite pad which was held in a No. 12 Buchner funnel. The filtrate was collected in a 19-liter solution bottle equipped with a vacuum take off. The mat was washed with 2 liters of ethyl acetate. The filtrate was transferred to a 20-liter separatory funnel and the phases allowed to separate. The ethyl acetate extract was removed and concentrated to approximately 1 liter in a laboratory-size glass circulating evaporator equipped with a continuous feed. The concentrate was evaporated further to a viscous oil in vacuo in a rotatory evaporator to yield 1.94 g of crude extract.

Step B: Liquid-Liquid Partition of Crude Extract

The crude extract from Step A (1.94 g) was dissolved in a mixture of 200 ml of methanol and 200 ml of Skellysolve B. The bi-phasic solution was transferred to a 1-liter separatory funnel and diluted with 22 ml of water. The mixture was shaken and the resultant phases allowed to separate. The aqueous methanol (lower phase) was transferred to a second 1-liter separatory funnel and extracted two more times with 200 ml aliquots of Skellysolve B. The Skellysolve B had previously been saturated with an equal volume of 10% water in methanol. The aqueous methanol phase was diluted with 44 ml of water and extracted three times with 200 ml portions of carbon tetrachloride. The carbon tetrachloride had previously been saturated with an equal volume of 25% water in methanol. The aqueous methanol phase was diluted with 41 ml of water and extracted three times with 200 ml portions of chloroform. The chloroform was previously saturated with an equal volume of 35% water in methanol. The carbon tetrachloride extracts were pooled and evaporated to dryness in vacuo in a rotatory evaporator to yield 595 mg of residue A. The chloroform extracts were pooled and evaporated to dryness in vacuo in a rotatory evaporator to yield 458 mg of residue B.

Step C: Trituration of Residues A and B

The residue A (547 mg) and residue B (389 mg) obtained in Step B were pooled and dissolved in 30 ml of 2 parts chloroform-1 part methanol. Dicalite (17.4 g) was added to the solution, and then a slurry was produced by the addition of 200 ml of Skellysolve B. The solvents were evaporated in vacuo with a rotatory evaporator. The residual powder was slurried in 500 ml of toluene and packed into a 4.1 cm I.D.×45.7 cm flash chromatography column. The Dicalite was packed into a bed with pressurized (N$_2$-5.7 psi) flow. When the packing solvent reached the bed surface, flow was stopped and the column de-pressurized. A layer of Ottawa sand (~2 cm) was added to the surface. The column was then eluted with pressurized nitrogen flow with the following elutropic series: toluene (500 ml); diethylether (500 ml); methylene chloride (500 ml); chloroform (500 ml); ethyl acetate (500 ml); acetonitrile (500 ml); tetrahydrofuran (500 ml) and methanol (500 ml). The toluene eluant and packing filtrate were combined (~1 liter) and evaporated to dryness in vacuo on a rotatory evaporator to yield 0.699 g of residue C.

Step D: Column Chromatography of Residue C

A 2.0 cm I.D.×30 cm Glenco column was slurry packed with 37 g of Woelm silica gel (0.060–0.200 mm, 70–230 mesh) in chloroform. Residue C (0.699 g) from Step C was dissolved in 5 ml of chloroform and applied to the top of the column. The sample was allowed to percolate into the packed bed. The void between the column top and silica gel bed was filled with standard Ottawa sand. The column was connected to a Glenco gradient elution apparatus and elution commenced with a 2-liter linear gradient of chloroform to 5% methanol in chloroform collecting 20×100 ml fractions. Each fraction was evaporated to dryness in vacuo in a rotatory evaporator. The residue was dissolved in 3 ml of 2 parts chloroform-1 part methanol. Aliquots (2 μl) of each fraction were spotted on Analtech silica gel GHLF thin layer chromatography (TLC) plates. The plates were eluted with 5% methanol in chloroform and visualized with 254 nm and 366 nm ultraviolet light. Fraction 6 was judged homogeneous. The crystalline residue from Fraction 6 was recrystallized from chloroform-methanol to yield 215 mg of sandramycin. This material was recrystallized from chloroform-methanol to yield 188 mg of pure sandramycin, mp. 208°–212° C.

Anal. Calc'd for $C_{60}H_{76}O_{16}N_{12}$ $8H_2O$: C, 52.78; H, 6.79; N, 12.31 Found: C, 52.58; H, 6.29; N, 12.29

EXAMPLE 3

Larger-Scale Isolation and Purification of Sandramycin

Step A: Extraction and Liquid Partition of Crude Extract

When the general isolation procedures described in Example 2, Steps A and B, were repeated, there was obtained 1.12 g of residue A and 3.03 g of residue B from the whole fermentation broth (~8 liters).

Step B: Trituration of Residues A and B

Residue A (1.12 g) obtained in Step A was dissolved in approximately 300 ml of 2 parts chloroform-1 part methanol. Dicalite (20 g) was added to the solution. The solvent was evaporator to dryness in vacuo in a rotatory evaporator. The residue was slurried in 300 ml of toluene and evaporated to dryness again. This was repeated a second time. The resultant residue was slurried in 300 ml of Skellysolve B and evaporated to dryness in a rotatory evaporator. This was repeated a second time. The Dicalite residue was slurried in 300 ml of Skellysolve B and packed into a 4.1 cm I.D.×45.7 cm flash chromatography column. The Dicalite was packed into a bed with a pressurized ($N_2$-5.7 psi) flow. A layer of Ottawa sand (~2 cm) was packed onto the bed. Elution commenced with pressurized nitrogen flow with the following elutropic series: Skellysolve B (500 ml); toluene (500 ml); diethyl ether (500 ml); methylene chloride (500 ml); chloroform (500 ml); ethyl acetate (500 ml); acetonitrile (500 ml); tetrahydrofuran (500 ml) and methanol (500 ml). The toluene eluant was evaporated to dryness in vacuo in a rotatory evaporator to yield 912.7 mg of residue D.

The general procedure outlined above was repeated except that the residue A utilized therein was replaced by 3.03 g of residue B, and there was thereby produced 766.7 mg of residue E from the toluene eluant.

The general procedures described above in Example 3, Steps A and B, were repeated except that the residues A and B obtained and utilized therein were replaced by 1.5 g and 1.97 g of residues A' and B', respectively, and there was thereby produced 993.9 mg of residue D' and 693 mg of residue E', respectively, from the toluene eluant.

Step C: Column Chromatography of Residues D and E

A 2.0 cm I.D.×30 cm Glenco column was slurry packed with 40 g of Woelm silica gel (0.063-0.200 mm, 70-230 mesh) in chloroform. The column was inserted into the medium pressure HPLC system and equilibrated with chloroform. Residues D, D', E and E' from Step B were pooled (approximately 3.366 g) and dissolved in 6 ml of chloroform. The solution was drawn into a 15-ml sample loop. The sample loop was inserted into the medium pressure HPLC system, and the sample was pumped onto the column with 200 ml of chloroform. Elution commenced with a 2-liter linear gradient of chloroform to 5% methanol in chloroform collecting 17×117 ml fractions. Aliquots (6 μl) from each fraction were assayed by TLC using 5% methanol in chloroform as eluant and visualized with 366 nm light. Fractions 5 and 6 were pooled and evaporated to dryness to yield 2.166 g of residue F. Fractions 7 through 12 were pooled and concentrated to dryness in vacuo with a rotatory evaporator. The residue (953 mg) was dissolved in 6 ml of chloroform and rechromatographed as above using a 2-liter linear gradient of chloroform to 1.5% methanol in chloroform collecting 20×100 ml fractions. Fractions 9 through 20 were pooled and evaporated to dryness in a rotatory evaporator to yield 860 mg of residue G.

Residues F and G were combined and recrystallized from chloroform-methanol to yield 1.985 g of pure sandramycin, which is identical to the product isolated in Example 2.

We claim:

1. An antitumor antibiotic sandramycin having the structural formula

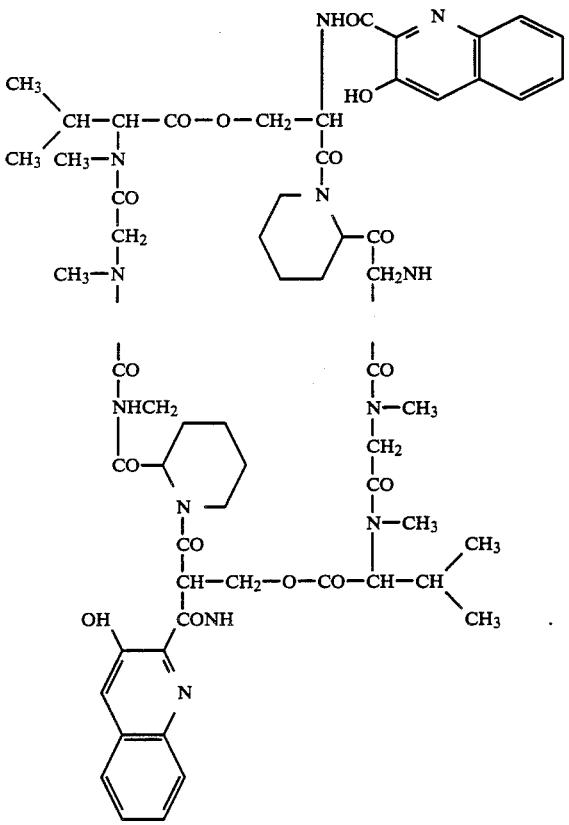

UNITED STATES PATENT AND TRADEMARK OFFICE
CERTIFICATE OF CORRECTION

PATENT NO. : 4,582,639
DATED      : April 15, 1986
INVENTOR(S) : James A. Matson et al.

It is certified that error appears in the above—identified patent and that said Letters Patent is hereby corrected as shown below:

The structural formula of Claim 1 should be shown as

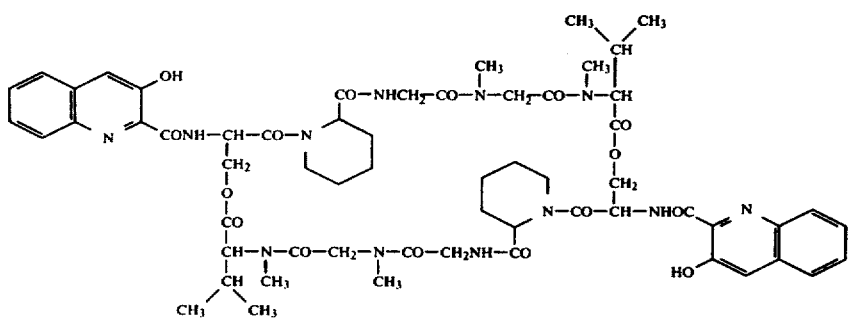

Signed and Sealed this

Twenty-ninth Day of July 1986

[SEAL]

Attest:

DONALD J. QUIGG

Attesting Officer    Commissioner of Patents and Trademarks